United States Patent [19]

Regelman

[11] Patent Number: 4,661,627

[45] Date of Patent: Apr. 28, 1987

[54] METHOD FOR SCAVENGING ACIDIC IMPURITIES FROM POLYMERIC ISOCYANATES

[75] Inventor: Dale F. Regelman, Wallingford, Conn.

[73] Assignee: The Dow Chemical Company, Midland, Mich.

[21] Appl. No.: 897,904

[22] Filed: Aug. 19, 1986

[51] Int. Cl.$^4$ ............................................. C07C 137/00
[52] U.S. Cl. ................................................... 560/352
[58] Field of Search ........................................ 560/352

[56] References Cited

U.S. PATENT DOCUMENTS

| | | | |
|---|---|---|---|
| 3,155,699 | 11/1964 | Powers | 260/453 |
| 3,179,680 | 4/1965 | Kober | 260/453 |
| 3,264,336 | 8/1966 | Powers | 260/453 |
| 3,373,182 | 3/1968 | Powers | 260/453 |
| 3,458,558 | 7/1969 | Cheng | 260/453 |
| 3,516,950 | 6/1970 | Haggis | 260/2.5 |
| 3,793,362 | 2/1974 | Kolakowski | 260/453 SP |
| 3,799,963 | 3/1974 | Adams | 560/352 |

FOREIGN PATENT DOCUMENTS

| | | |
|---|---|---|
| 727137 | 2/1966 | Canada . |
| 1229181 | 4/1971 | United Kingdom . |
| 1417075 | 12/1975 | United Kingdom ............. 560/352 |

*Primary Examiner*—Alan Siegel
*Attorney, Agent, or Firm*—J. S. Rose

[57] ABSTRACT

Disclosed is a process for reducing the acid content and thereby increasing the reactivity of a polymethylene polyphenylisocyanate which comprises contacting said polyisocyanate with an effective amount of a poly(N-vinylimidazole).

9 Claims, No Drawings

METHOD FOR SCAVENGING ACIDIC IMPURITIES FROM POLYMERIC ISOCYANATES

FIELD OF THE INVENTION

This invention relates to polymeric organic isocyanates and more particularly to a novel process for reducing acidic impurities in polymethylene polyphenylisocyanates.

DESCRIPTION OF THE PRIOR ART

The majority of commercially available organic isocyanates are prepared by processes which comprise phosgenation of an amine compound. The isocyanate products obtained by phosgenation methods are generally contaminated with hydrogen chloride and a wide variety of by-products containing hydrolyzable chloride atoms; the latter being susceptible to conversion to free hydrogen chloride. Significant concentrations of such contaminants result in product acidity and adversely affect reactivity rates of the isocyanate.

Innumerable methods have been described for reducing acidity and/or hydrolyzable chloride concentrations in organic isocyanates. For example, a number of methods have been described which comprise treatment of the isocyanate with metals such as copper, silver, nickel, iron, zinc, cobalt, aluminum, bismuth, and the like; halide salts of such metals; and organic complexes of such metals, see for example U.S. Pat. Nos. 3,155,699; 3,264,336; 3,373,182 and 3,458,558. Following treatment in accord with such methods, it is often necessary to effect a separation of the isocyanate from the reaction by-products of the treatment, i.e. metal salts and complexes. This is accomplished by distillation of the treatment product.

Fractional distillation of isocyanates has been described as a method for removing undesired acid contaminants from isocyanates (U.S. Pat. No. 3,264,336).

Recrystallization of diisocyanates is suggested for reducing hydrolyzable chloride levels in such compounds by British Pat. No. 1,229,181.

Reduction of hydrolyzable chloride (without a reduction of acidity) in isocyanates by a method of chloride hydrolysis is described in U.S. Pat. No. 3,179,680 and in Canadian Pat. No. 727,137. The acidity can be reduced concurrently by volatilization of hydrogen chloride present, using conventional methods, for example by passing a stream of inert gas through the isocyanate mixture while heating to a temperature circa 150° C. to 220° C. (see U.S. Pat. No. 3,516,950).

In all of the above described methods, the isocyanate is exposed to substantially high temperature ranges for extended periods of time, either during the process of treatment or during post-process separative steps necessitated by the treatment.

Polymethylene polyphenylisocyanates as a class are sensitive to heat, and any substantial heating of the polyisocyanate results in polymerization and consequent viscosity build-ups. Also, when heating is carried out in the presence of a number of metals and metallic salts such as, for example, the iron, copper and tin materials employed in the above described methods of U.S. Pat. Nos. 3,155,699; 3,264,366; 3,373,182 and 3,458,558, polymerization rates are increased. Polymerization of the polyisocyanate with consequent viscosity build-up is sometimes undesirable, limiting the uses for which the polyisocyanate can be employed.

It has been suggested that acid levels in crude polyarylpolyisocyanate compositions could be lowered by the addition of lime to the isocyanate. In theory, this could be accomplished without heating the isocyanate. However, lime is not readily soluble in polymethylene polyphenylisocyanates, and its effectiveness in lowering acidity without heating is drastically reduced. U.S. Pat. No. 3,793,362 teaches the use of epoxides in lowering acidity but the epoxide reaction products remain in the polyisocyanate.

I have now found that the acidity content of polymethylene polyphenylisocyanates can be greatly reduced with virtually no increase in product viscosity by treatment of the isocyanates with a minor proportion of an insoluble poly(N-vinylimidazole). The direct result is an isocyanate having dramatically increased isocyanate reactivity in the various isocyanate poly-addition reactions. For example, the treated isocyanates can be used to prepare polyurethane and polyisocyanurate polymers including foams having shorter reaction times, gel times, foam rise profiles, and the like.

SUMMARY OF THE INVENTION

This invention comprises a process for reducing the acid content and thereby increasing the reactivity of a polymethylene polyphenylisocyanate (PAPI) which comprises contacting said polyisocyanate with an effective amount of a poly(N-vinylimidazole).

The term "acid content" refers to free hydrogen chloride and strongly ionic, covalent bonded chlorine present in the isocyanate.

The term "effective amount" means an amount sufficient to reduce the acidity and thereby effect an increase in isocyanate reactivity in polyaddition reactions such as polyurethane and polyisocyanurate formation.

DETAILED DESCRIPTION OF THE INVENTION

The process of the invention is carried out by contacting the poly(N-vinylimidazole) [hereinafter PVI] with the polymethylene polyphenylisocyanate, using any conventional and appropriate equipment for contacting, mixing, or stirring liquids and solids together. Thus, mixing of the two materials can be carried out with any conventional blending equipment. When small quantities of polyisocyanate are to be treated, mixing is readily accomplished by hand or manual stirring. When treating large quantities of polyisocyanate, it is advantageous to employ any of the powered blending devices commonly employed in mixing liquids/liquids or liquids/solids. The present process also contemplates optional embodiments wherein the liquid polyisocyanate is passed through a bed of the PVI either in a single pass or as a continuous or recycle procedure. However, the insoluble PVI is readily and efficiently removed from the polyisocyanate using conventional filtration procedures. Accordingly, the preferred method of contacting the ingredients is simply by mixing them together using the above described procedures followed by filtration to remove the PVI.

The temperature at which the mixing can be carried out is not critical in itself in terms of the effectiveness of removal of the acid impurities. However, one of the significant benefits of the present process is the fact that elevated temperatures are not required. In fact, as discussed above, elevated temperatures can lead to viscosity build-up in the isocyanate and preferably are to be avoided. The contacting of the isocyanate with the PVI is advantageously conducted at about −10° C. to about 100° C., preferably, from about 20° C. to about 50° C., and, most preferably, from about 20° C. to about 30° C.

In respect of the actual contact time, this will vary according to the levels of acidic impurities present, isocyanate viscosity, activity of the PVI, whether the preferred static mixing procedure is employed or a continuous method, and the like. The present method is not meant to be limited by a specific contact time but solely by a time sufficient to reduce the acidity level of the polyisocyanate and/or to effect an increase in isocyanate reactivity in isocyanate poly-addition reactions.

Generally speaking, the contact time will be for at least 2 minutes, advantageously from about 2 minutes to about 8 hours, preferably from about 10 minutes to about 1 hour.

Isocyanates, in general, are susceptible to reaction with moisture. For this reason, most mixing operations of polyisocyanate with the PVI are preferably carried out in a dry atmosphere and preferably under an inert gas atmosphere, such as nitrogen or argon.

The PVI employed can be any poly(N-vinylimidazole) polymer obtained from the olefinic polymerization of an N-vinylimidazole or substituted vinylimidazole using known methods for preparing such vinyl polymers. Typically, the monomer can be polymerized in an aromatic solvent such as benzene using a free-radical initiator, for example, azobis(isobutyronitrile). The PVI precipitates from the solution and is readily isolated by filtration. The general procedure is disclosed in such polymer references as "Macromolecules" 1981, 14, pp. 1700 to 1706. Alternatively, "Macromolecules" 1980, 13, pp. 1375 to 1381 discloses an aqueous preparation wherein the N-vinylimidazole is polymerized in water at 95° C. using, 4,4'-azobis(4-cyanovaleric acid) as the initiator. Although the imidazole ring may be substituted with inert substituents such as lower alkyl of $C_1$ to $C_4$; halogen of chlorine, fluorine, bromine, and iodine; lower-alkoxy of $C_1$ to $C_4$; preferred is the PVI obtained from the unsubstituted N-vinylimidazole.

The PVI is not limited as to molecular weight range in respect of its effectiveness in removing the acidic impurities from the isocyanate. Generally speaking though, the weight average molecular weight ($\bar{M}_w$) will fall within a range of from about 25,000 to about 1,500,000, more often it will be from about 50,000 to about 1,000,000.

Surprisingly, the imidazole must be in polymeric form to be effective in removing acidic impurities. When monomers are employed, it results in the polymerization of the polyisocyanate which is a known function of imidazole compounds; see Examples below.

Generally speaking, the PVI polymers are soluble in protic solvents, for example water, methanol, ethanol, isopropanol, n-butanol, iso-butyl alcohol, and the like; and insoluble in aromatic, aliphatic, and cycloaliphatic solvents such as benzene, toluene, hexane, cyclohexane, and the like.

The PVI polymers are preferably employed in finely divided solid form which, advantageously, is the form in which they are obtained when prepared in aromatic solvents.

Although not wishing the present invention to be limited by any theoretical considerations but only by the claims appended hereinbelow, it is believed that the imidazole ring acts as a basic substance to interact with the acidic impurities in the isocyanate. That is to say, the imidazole ring becomes protonated thereby removing said impurities. Both the PVI and impurities are then completely separated from the isocyanate upon filtration.

If each and every imidazole ring in the PVI polymers was 100 percent effective in neutralizing hydrogen chloride, then the exact amount required to neutralize each acid equivalent in the PAPI would be easily calculated based on the calculated equivalent weight of any PVI which would equal the mer unit weight. However, it has been determined that every imidazole ring in the polymer does not absorb a hydrogen chloride molecule for whatever reason. Accordingly, it has been found most expedient to employ the PVI in the proportions of from about 0.1 to about 20 percent by weight of the PAPI, preferably, from about 0.5 to about 10 percent, and, most preferably, from about 1 to about 5 percent.

The polymethylene polyphenylisocyanates which can be treated in accordance with the present invention are fully described and exemplified in the U.S. patents cited supra, particularly U.S. Pat. No. 3,793,362, whose disclosure relative thereto is incorporated herein by reference.

A preferred polymethylene polyphenylisocyanate for purification using the present method contains from about 20 to about 85 percent by weight of methylenebis(phenyl isocyanate) with the balance being polymethylene polyphenylisocyanates having functionalities greater than 2. The methylenebis(phenyl isocyanate) can be at least 95 percent 4,4'-isomer or it can include from 0 to 70 percent of the 2,4'-isomer, and 0 to 10 percent of the 2,2'-isomer.

The surprising features of the present process include the ease with which the isocyanate reactivity of PAPI mixtures can be increased simply by being mixed at ambient temperatures for very short periods with the PVI; the fact that the PVI is so easily removed from the PAPI as opposed to prior art methods where the neutralizing ingredients must remain in the PAPI; and the fact that the PVI has little or no effect on isocyanate viscosity, whereas the imidazole ring in non-polymer form acts as a catalyst in polymerizing the isocyanate to, presumably, polyisocyanurate.

The polymethylene polyphenylisocyanates purified in accordance with the present invention find utility in the preparation of solid polyurethane moldings, castings, and cellular foams and in the preparation of their polyisocyanurate counterparts when the organic polyol is reduced and trimerization catalysts are employed.

The following examples describe the manner and process of making and using the invention and set forth the best mode contemplated by the inventor of carrying out the invention but are not to be construed as limiting.

Preparation of Poly(N-vinylimidazole) (PVI)

A one-liter resin flask was charged with 50 g. of N-vinylimidazole (supplied by Aldrich Chemical Company), 300 ml. of toluene, and 0.50 g. of azobis(isobutyronitrile). Under a positive stream of nitrogen and at 60° C. the solution was stirred. After about 3.5 hours the solution was cloudy and after 18 hours a heavy precipitate had formed. Stirring was continued at 60° C. for a total period of 24 hours.

The cooled reaction mixture was poured into about 2000 ml. of toluene and the white powdery polymer product was collected by suction filtration. It was dried under vacuum; wt.=45.2 g.; $\eta_{inh}$ (0.5 percent solution in methanol)=0.65.

EXAMPLES 1 THROUGH 6

The following examples describe the preparation of six polymethylene polyphenylisocyanate (PAPI) compositions in accordance with the present process and a comparison of their isocyanate reactivities compared with two control PAPI compositions (Control 1 and 2) not treated by the present method.

In Example 1, 150 g. of a PAPI sample identified as Isocyanate I, and described in Footnote 1 of Table I below, was stirred in a 500 ml. resin kettle under a positive argon pressure with 7.5 g. of the PVI powder prepared above. Stirring was continued at ambient room temperature (about 20° C.) for one hour.

The PVI was removed by suction filtration providing a PAPI identified as Isocyanate Ia in Table I; viscosity (cps at 25° C.)=67 (c.f. value of 67 cps for Isocyanate I).

A solid polyurethane was prepared from a 47 g. sample of the Isocyanate Ia by manually mixing it in a beaker with a B side component containing 50 g. of a polyoxypropylene-polyoxyethylene triol having a hydroxyl weight of 2000, 10 g. of ethylene glycol, and 0.06 g. of dibutyltin dilaurate. The time was measured to gelation by the rapid increase in viscosity observed during stirring and just prior to complete solid polyurethane formation. The gel time was 26 seconds. A Control 1 polyurethane was formed by repeating the above preparation but replacing the Isocyanate Ia with the untreated Isocyanate I. A gel time of 392 seconds was observed.

Examples 2 and 3 through 6 were carried out identically to Example 1 by mixing respectively Isocyanate I and Isocyanate II (defined below) with the requisite proportions by weight of PVI and for the contact times noted in Table I to yield the Isocyanate Ib and Isocyanates IIa to IId. Control 2 represents the untreated Isocyanate II. Each polyisocyanate was tested for its gel time using the identical procedure and ingredients set forth above except for using the appropriate polyisocyanate sample. Gel times for the respective polyisocyanates are set forth in Table I.

Both Control 1 and 2 showed very much longer gel times when compared with their counterparts treated with the PVI. Example 6 employed only 0.1 percent by weight of PVI. However, its gel time was still at least 30 percent faster than the Control 2 material.

Example 2 showed that treatment of Isocyanate I with the PVI did not affect the material with time as the observed viscosity after one month was virtually identical with the Control 1 viscosity (65 cps vs 67 cps).

In another comparison test, 300 g. of the Isocyanate 1 was mixed with 3 g. of N-methylimidazole under the same conditions above for Examples 1 through 6. An immediate skin formed on the isocyanate and after 45 minutes the sample had become a brown viscous paste. Clearly, the monomeric imidazole was acting as an isocyanate trimerization catalyst and therefore behaved differently from the polymeric PVI.

Another comparison in isocyanate reactivity was measured by preparing hand-mix polyurethane foam samples from Isocyanate II and IIa and measuring their respective foam rise profiles.

The foam formulation employed had 140 parts of Isocyanate II or IIa along with 16 parts of monofluorotrichloromethane in an A side and a B side containing 211 parts of a Terate 211 polyester polyol having an OH eq. wt.=120 (supplied by Hercules Chemical Company), 1.5 parts of DC 193 (a silicone surfactant supplied by Dow Corning, Midland, Michigan), 1.5 parts of DABCO 33LV (urethane catalyst supplied by Air Products Inc.), and 20 parts of monofluorotrichloromethane. The A and B side ingredients were mixed for 30 seconds in a 1 quart cup using a drill press motor equipped with a Con high shear mixing blade and the rise profile measured as follows:

| Rise time (minutes:seconds) | Isocyanate II | Isocyanate IIa |
|---|---|---|
| Initiation | 1:25 | 1:00 |
| Gel | 2:40 | 1:55 |
| Rise | 3:30 | 2:55 |

Clearly the isocyanate treated according to the present method had a much faster foam rise profile.

TABLE I

| Example | Control 1 | 1 | 2 | Control 2 | 3 | 4 | 5 | 6 |
|---|---|---|---|---|---|---|---|---|
| Isocyanate | I[1] | Ia | Ib | II[2] | IIa | IIb | IIc | IId |
| PVI Conc. (% by wt.) | — | 5 | 1 | — | 1 | 1 | 0.5 | 0.1 |
| Contact Time (hrs.) | — | 1 | 18 | — | 18 | 2 mins. | 6 | 6 |
| Gel Time (secs.) | 392 | 26 | 25 | 292 | 25 | 33 | 29 | 197 |
| Viscosity (cps. at 25° C.) | 67 | 67 | 65[3] | — | — | — | — | — |

Footnotes to Table I
[1]Isocyanate I: A polymethylene poly (phenyl isocyanate) mixture containing about 65 percent by weight of methylenebis (phenyl isocyanate) with the balance being isocyanates of functionality greater than 2 and wherein the MDI contains about 12 percent o,p'-isomer; isocyanate eq. wt. = 131; acidity = 0.03%.
[2]Isocyanate II: A polymethylene poly (phenyl isocyanate) mixture containing about 45 percent by weight of MDI with the balance being isocyanates of functionality greater than 2; isocyanate eq. wt. = 133; acidity = 0.05%.
[3]Viscosity after about 1 month storage = 69 cps.

I claim:

1. A process for reducing the acid content of a polymethylene polyphenylisocyanate which comprises contacting said polyisocyanate with an effective amount of a poly(N-vinylimidazole).

2. A process according to claim 1 wherein said contacting is carried out at a temperature of from about −10° C. to about 100° C.

3. A process according to claim 2 wherein the temperature is from about 20° C. to about 30° C.

4. A process according to claim 1 wherein said effective amount comprises from about 0.1 to about 20 percent by weight of poly(N-vinylimidazole) based on the combined weight of the latter and said polyisocyanate.

5. A process according to claim 4 wherein said effective amount is from about 0.5 to about 10 percent by weight.

6. A process according to claim 1 wherein said polyisocyanate contains from about 20 to about 85 percent by weight of methylenebis(phenyl isocyanate) and the balance being polymethylene polyphenylisocyanates having functionalities greater than 2.

7. A process according to claim 1 wherein said poly(N-vinylimidazole) has an $\overline{M}_w$ of about 50,000 to about 1,000,000.

8. A process according to claim 1 wherein said contacting is carried out for at least 2 minutes.

9. A process for reducing the acid content of a polymethylene polyphenylisocyanate containing from about 20 to about 85 percent by weight of methylenebis(phenyl isocyanate) and the balance being polymethylene polyphenylisocyanates having functionalities greater than 2 said process comprising contacting said polyisocyanate with from about 0.5 to about 10 percent by weight of a poly(N-vinylimidazole) at a temperature of from about 20° C. to about 30° C.

* * * * *